United States Patent [19] [11] Patent Number: 4,645,737
Coates et al. [45] Date of Patent: * Feb. 24, 1987

[54] ENZYME/IMMUNOFLUORESCENT ASSAY FOR ANTI-TREPONEMAL ANTIBODIES

[75] Inventors: Stephen R. Coates, Lafayette; Walter L. Binder, San Diego, both of Calif.

[73] Assignee: American Hoechst Corporation, Somerville, N.J.

[ * ] Notice: The portion of the term of this patent subsequent to Dec. 11, 2001 has been disclaimed.

[21] Appl. No.: 586,538

[22] Filed: Mar. 5, 1984

[51] Int. Cl.$^4$ .................. G01N 33/53; G01N 33/534; G01N 33/535; G01N 33/571
[52] U.S. Cl. .......................... 435/7; 435/28; 436/511
[58] Field of Search .................. 435/7, 28; 436/511

[56] References Cited

U.S. PATENT DOCUMENTS 4,041,146  8/1977  Gaever .
4,144,031  3/1979  Acevedo .
4,228,127 10/1980  Acevedo .
4,288,426  9/1981  Stevens .
4,487,830 12/1984  Coates et al. .......................... 435/7

FOREIGN PATENT DOCUMENTS 2067286  7/1981  United Kingdom .

Primary Examiner—Sidney Marantz
Attorney, Agent, or Firm—Jerome Rosenstock

[57] ABSTRACT

A method for the determination of anti-treponemal antibody in a test sample comprises contacting a substrate for the anti-treponemal antibody with sample; treating the contacted substrate with labeled antihuman Ig antibody selected from (a) a mixture comprising enzyme labeled antihuman Ig antibody and fluorescent labeled antihuman Ig antibody, (b) antihuman Ig antibody labeled with an enzyme and a fluorescent label, and (c) fluorescent labeled antihuman Ig antibody to which enzyme labeled antibody against the animal species from which the antibody used in the fluorescent labeled antibody was derived is added subsequently, and (d) enzyme labeled antihuman Ig antibody to which fluorescent labeled antibody against the animal species from which the antibody used in the enzyme labeled antibody was derived is subsequently added; determining the enzyme activity of the treated substrate; and determining the immunofluorescent patterns in substrates exhibiting enzyme activity. The method is useful for the rapid screening of anti-treponemal antibodies for the diagnosis of syphilis.

16 Claims, No Drawings

ENZYME/IMMUNOFLUORESCENT ASSAY FOR ANTI-TREPONEMAL ANTIBODIES

BACKGROUND OF THE INVENTION

Immunofluorescence is routinely employed in testing human serum for the presence of anti-treponemal antibodies associated with syphilis. The immunofluorescent antibody technique consists of two antigen—antibody reactions. The first reaction takes place between anti-treponemal antibody contained in the serum sample and specific antigen localized in a particular substrate. The second reaction is between the anti-treponemal antibody/antigen complex and antihuman immunoglobin (Ig) antibody that has been tagged with a fluorescent label. After the second reaction, the substrate is examined for fluorescence using the fluorescent microscope. In positive samples, the patterns of fluorescence are used as indicators for additional tests.

In spite of its accuracy and ease of use, the immunofluorescent antibody technique has one major disadvantage. It does not allow for quick screening of a number of serum samples since each sample must be individually studied under a fluorescent microscope to ascertain whether the serum is positive or negative. Since the majority of sera routinely tested are negative for anti-treponemal antibody, the advantages of a method which would eliminate microscopic examination of negative sera are obvious. Such a method would be less labor intensive and therefore less expensive.

It is an object of the present invention to provide a fast and accurate method of screening a large number of serum samples for anti-treponemal antibody, which, when present, can be further confirmed by fluorescent microscopy.

SUMMARY OF THE INVENTION

The present invention relates to a method for the determination of anti-treponemal antibodies. More particularly, the invention relates to a single assay method that can be used to screen quickly test samples for the presence of anti-treponemal antibody and then confirm the presence of detected anti-treponemal antibody. The unique feature of the method of the present invention resides in tagging the complex of anti-treponemal antibody and specific antigen with antihuman immunoglobin which has been tagged with both an enzyme label and a fluorescent label. It is this dual labeling that enables the assay method to be used for both detection and confirmation of the presence of anti-treponemal antibodies.

In summary, the present invention relates to a method for the determination of anti-treponemal antibody in a test sample, comprising:
providing a substrate for said anti-treponemal antibody;
contacting said substrate with test sample;
treating said contacted substrate with labeled antihuman immunoglobulin (Ig) antibody, said labeled antihuman antibody selected from the group consisting of:
(a) a mixture comprising enzyme labeled antihuman Ig antibody and fluorescent labeled antihuman Ig antibody;
(b) antihuman Ig antibody labeled and with an enzyme and a fluorescent label;
(c) fluorescent labeled antihuman Ig antibody to which enzyme labeled antibody against the animal species from which the antibody used in the fluorescent labeled antibody was derived is subsequently added; and
(d) enzyme labeled antihuman Ig antibody to which fluorescent labeled antibody against the animal species from which the antibody used in the enzyme labeled antibody was derived is subsequently added.
analyzing the treated substrate to determine whether it has an enzyme activity; and
determining the immunofluorescent pattern of a resultant enzyme active substrate.

A first preferred aspect of the present invention relates to that embodiment wherein the labeled antihuman Ig antibody is a mixture comprising enzyme labeled antihuman Ig antibody and fluorescent labeled antihuman antibody.

A second preferred aspect of the present invention relates to that embodiment wherein the antihuman Ig antibody is labeled with both an enzyme and a fluorescent label.

A third preferred aspect of the present invention relates to that embodiment wherein the labeled antihuman Ig antibody is fluorescent labeled antihuman Ig antibody to which enzyme labeled antibody against the animal species from which the antibody used in the fluorescent labeled antibody was derived is subsequently added.

DETAILED DESCRIPTION

Antibodies determined by the method of the present invention are useful as an aid in the diagnosis of syphilis.

The detection of anti-treponemal antibodies according to the present invention is accomplished by contacting a suitable antigen substrate with test specimen; treating the contacted substrate with labeled antihuman immunoglobulin (Ig) antibody, said labeled antibody selected from he group consisting of (a) a mixture comprising enzyme labeled antibody and fluorescent labeled antibody, (b) antihuman antibody labeled with an enzyme and a fluorescent label, (c) fluorescent labeled antihuman Ig antibody to which enzyme labeled antibody against the animal species from which the antibody used in the fluorescent labeled antibody was derived is subsequently added, and (d) enzyme labeled antihuman Ig antibody to which fluorescent labeled antibody against the animal species from which the antibody used in the enzyme labeled antibody was derived is subsequently added; determining the enzyme activity of the treated substrate; and determining the immunofluorescent pattern of substrates exhibiting enzyme activity.

Substrates suitable for use in the present invention include Treponema pallidum. The substrate contains the antigen used to determine the presence of anti-treponemal antibody in the test specimen. For best results, it is advisable that the substrate material containing the antigen be prepared in such a way as to preserve antigenic determinants. This means that fixatives are best avoided, or used only with caution.

Substrates utilized herein are preferably supported on flat, transparent surfaces to facilitate the determination of immunofluorescent patterns. Particularly suitable support surfaces are afforded by tissue culture treated microtiter plates. Such plates preferably have a well bottom thickness of less than 0.5 mm which allows one to use high magnification objectives in examining the substrate.

Labeled antihuman Ig antibody, used to tag the complex of antibody and substrate antigen, is selected from one of the following categories:
(a) a mixture comprising enzyme labeled antihuman Ig antibody and fluorescent labeled antihuman Ig antibody;
(b) antihuman Ig antibody labeled with an enzyme and a fluorescent label;
(c) fluorescent antihuman Ig antibody to which enzyme labeled antibody against the animal species from which the antibody used in fluorescent labeled antibody was derived is subsequently added; and
(d) enzyme labeled antihuman Ig antibody to which fluorescent labeled antibody against the animal species from which the antibody used in the enzyme labeled antibody was derived is subsequently added.

Fluorochrome conjugated antisera, utilized as enzyme labeled antihuman Ig antibody herein, are available commercially or may be readily prepared by methods well known in the art. Enzymes that are particularly preferred as labeling agents include, for example, horeseradish peroxidase, alkaline phosphatase, glucose oxidase, lactoperoxidase and β-galactosidase.

In an alternative mode, antihuman Ig antibody labeled with both an enzyme and a fluorescent label is used in lieu of a mixture comprising enzyme labeled antihuman Ig antibody and fluorescent labeled antihuman Ig antibody. Fluorochrome/enzyme conjugated antisera are readily prepared by reacting a commercially available enzyme/fluorochrome conjugate with a suitably purified immunoglobulin fraction.

In another alternative mode, fluorescent labeled antihuman Ig antibody is employed. After washing the plate, enzyme labeled antibody against the animal species from which the antibody used in the fluorescent labeled antibody was derived is then added and allowed to combine with any attached fluorescent labeled antihuman Ig antibody. The labeled antibodies are available commercially or may be readily prepared by methods well known in the art. Particularly preferred are enzyme labeled goat anti-rabbit IgG after fluorescein-labeled rabbit anti-human Ig.

In another alternative mode, enzyme labeled antihuman Ig antibody is employed. After washing the plate, fluorescent labeled antibody against the animal species from which the antibody used in the enzyme labeled antibody was derived is then added and allowed to combine with any attached fluorescent labeled antihuman Ig antibody. The labeled antibodies are available commercially or may be readily prepared by methods well known in the art. Particularly preferred are fluorescein-labeled goat anti-rabbit IgG after enzyme labeled rabbit anti-human Ig.

In practicing the method of the present invention, the antigen substrate, the test sample suspected of containing anti-treponemal antibody and the labeled antihuman Ig antibody are combined and handled as discussed below.

Antigen substrate for the anti-treponemal antibody is contacted at room temperature with test sample suspected of containing the anti-treponemal antibody. The period of contact is from 30 minutes to one hour. If the test sample contains anti-treponemal antibody specific for the antigen localized in the substrate, a substrate, a substrate bound anti-treponemal antibody/antigen complex if formed. After repeated washings, the contacted substrate is treated with labeled antihuman Ig antibody selected from the group consisting of (a) a mixture comprising enzyme labeled antihuman Ig antibody and fluorescent labeled antihuman Ig antibody, (b) antihuman Ig antibody labeled with an enzyme and a fluorescent label, (c) fluorescent labeled antihuman Ig antibody to which enzyme labeled antibody against the animal species from which the antibody used in the fluorescent labeled antibody was derived is subsequently added, and (d) enzyme labeled antihuman Ig antibody to which fluorescent labeled antibody against the animal species from which the antibody used in the enzyme labeled antibody was derived is subsequently added. Treatment of the substrate with labeled antibody is typically carried out at room temperature a period of 30 minutes to one hour. If the treated substrate contains bound anti-treponemal antibody, a labeled substrate is formed at this stage. After repeated washings, the enzyme activity of the substrate is determined by the addition of a specific substrate for the enzyme. A variety of substrates suitable for enzymes recited and employed herein can be found in Bergmeyer, *Methods of Enzymatic Analysis*, Academic Press, New York, 1965.

The presence of enzyme activity in the substrate can be determined visually and spectrophotometrically. In the first instance, the substrate is simply examined visually for color produced by the enzymatic cleavage of the enzyme substrate (chromogen). In the second instance, the optical density of the chromogen solution is determined and correlated with anti-treponemal antibody titer which is an estimation of the amount of anti-treponemal antibody in the test sample. Thus, the use of an enzyme label in the method of the present invention allows the method to be employed as either a qualitative or quantitative test for the determination of anti-treponemal antibody.

Test samples which exhibit enzymatic activity are confirmed as to the presence of anti-treponemal antibodies by direct examination using a fluorescent microscope with an epi illumination system to determine the immunofluorescent pattern, by inverting the microtiter plate and viewing through the bottom.

What is claimed is:
1. A method for the determination of anti-treponemal antibody in a test sample, comprising:
providing a substrate for the anti-treponemal antibody; contacting said substrate with a test sample; treating said contacted substrate with labeled antihuman immunoglobulin antibody, said labeled antihuman immunoglobulin antibody selected from the group consisting of:
(a) a mixture comprising enzyme labeled antihuman immunoglobulin antibody and fluorescent labeled antihuman immunoglobulin antibody;
(b) antihuman immunoglobulin antibody labeled with an enzyme and a fluorescent label;
(c) fluorescent labeled antihuman immunoglobulin antibody to which enzyme labeled antibody against the animal species from which the antibody used in the fluorescent labeled antibody was derived is subsequently added; and
(d) enzyme labeled antihuman immunoglobulin antibody to which fluorescent labeled antibody against the animal species from which the antibody used in the fluorescent labeled antibody was derived is subsequently added;

analyzing of the treated substrate to determine if it has enzyme activity; and determining the immunofluorescent pattern in substrates exhibiting enzyme activity.

2. The method according to claim 1 wherein said labeled antihuman antibody comprises (a).

3. The method according to claim 1 wherein said labeled antihuman antibody comprises (b).

4. The method according to claim 1 wherein said labeled antihuman antibody comprises (c).

5. The method according to claim 1 wherein said labeled antihuman antibody comprises (d).

6. The method according to claim 2 wherein said enzyme is horseradish peroxidase.

7. The method according to claim 3 wherein said enzyme is horseradish peroxidase.

8. The method according to claim 3 wherein said enzyme is horseradish peroxidase.

9. The method according to claim 2 wherein said fluorescent label is fluorescein.

10. The method according to claim 3 wherein said fluorescent label is fluorescein.

11. The method according to claim 4 wherein said fluorescent label is fluorescein.

12. The method according to claim 2 wherein said enzyme is horseradish peroxidase and said fluorescent label is fluorescein.

13. The method according to claim 3 wherein said enzyme is horseradish peroxidase and said fluorescent label is fluorescein.

14. The method according to claim 4 wherein said enzyme is horseradish peroxidase and said fluorescent label is fluorescein.

15. The method according to claim 1 wherein said antihuman antibody is antihuman IgG.

16. The method according to claim 1 wherein said substrate comprises Treponema pallidum cells.

* * * * *